(12) United States Patent
Montanari et al.

(10) Patent No.: US 12,329,542 B2
(45) Date of Patent: Jun. 17, 2025

(54) SENSING

(71) Applicant: Omnibuds Ltd, Cambridge, GA (US)

(72) Inventors: Alessandro Montanari, Cambridge (GB); Fahim Kawsar, Cambridge (GB); Andrea Ferlini, Cambridge (GB)

(73) Assignee: OMNIBUDS LTD, Cambridge (GB)

( * ) Notice: Subject to any disclaimer, the term of this patent is extended or adjusted under 35 U.S.C. 154(b) by 215 days.

(21) Appl. No.: 17/892,806

(22) Filed: Aug. 22, 2022

(65) Prior Publication Data
US 2023/0057740 A1 Feb. 23, 2023

(30) Foreign Application Priority Data
Aug. 23, 2021 (EP) .................................... 21192515

(51) Int. Cl.
A61B 5/00 (2006.01)
(52) U.S. Cl.
CPC .......... *A61B 5/7221* (2013.01); *A61B 5/7235* (2013.01)
(58) Field of Classification Search
CPC .............. A61B 5/7221; A61B 5/7235; A61B 5/1118; A61B 5/327; A61B 2562/0219; A61B 5/721; A61B 5/02438; A61B 2505/09; A61B 5/725
See application file for complete search history.

(56) References Cited

U.S. PATENT DOCUMENTS

| | | | |
|---|---|---|---|
| 8,775,120 B2 | 7/2014 | Molettiere et al. | |
| 9,001,229 B2 | 4/2015 | Goh et al. | |
| 9,685,171 B1 | 6/2017 | Yang | |
| 10,043,261 B2 | 8/2018 | Bhaskar et al. | |
| 10,061,891 B2 | 8/2018 | Grundlehner et al. | |
| 10,306,224 B2 | 5/2019 | Kondo | |
| 10,356,179 B2 * | 7/2019 | Fink | H04L 65/80 |

(Continued)

FOREIGN PATENT DOCUMENTS

| | | |
|---|---|---|
| EP | 3182407 B1 | 6/2017 |
| KR | 101 483 756 B1 | 1/2015 |
| WO | WO 2018/004614 A1 | 1/2018 |

OTHER PUBLICATIONS

Bosch, "Bosch Programmable Sensor Systems", Retrieved on Mar. 21, 2023, Retrieved via the Wayback Machine <URL:https://web.archive.org/web/20210627194429/https://www.bosch-sensortec.com/products/smart-sensors/programmable-sensor-systems/>, (Jun. 27, 2021), 7 pages.

(Continued)

*Primary Examiner* — Manuel A Rivera Vargas
(74) *Attorney, Agent, or Firm* — ALSTON & BIRD LLP

(57) ABSTRACT

A method is provided that includes determining a quality of a data portion of an input sensor data stream based, at least in part, on data of a first data type and determining between, at least, generation of two or more streams of a second, different data type including at least one synthesised data stream of the second data type. Determining between generation of two or more streams of a second, different data type is based, at least in part, on the determined quality. The synthesis is based, at least in part, on the data of the first data type. The method further includes causing generation of at least one stream of the second, different data type based, at least in part, on the determination between generation of two or more streams of the second, different data type.

20 Claims, 5 Drawing Sheets

(56) References Cited

U.S. PATENT DOCUMENTS

| | | | |
|---|---|---|---|
| 10,395,356 | B2 | 8/2019 | Zhang et al. |
| 10,460,235 | B1 | 10/2019 | Truong et al. |
| 10,592,386 | B2 | 3/2020 | Walters et al. |
| 10,713,294 | B2 | 7/2020 | Kim et al. |
| 10,973,423 | B2 | 4/2021 | Jain et al. |
| 11,229,403 | B2 * | 1/2022 | Smital .................. A61B 5/7221 |
| 2009/0054752 | A1 | 2/2009 | Jonnalagadda et al. |
| 2014/0156228 | A1 * | 6/2014 | Molettiere ............. G16H 10/60 702/189 |
| 2015/0196256 | A1 | 7/2015 | Venkatraman et al. |
| 2016/0206247 | A1 | 7/2016 | Morland et al. |
| 2016/0361021 | A1 | 12/2016 | Salehizadeh et al. |
| 2016/0367198 | A1 | 12/2016 | Chon et al. |
| 2017/0164847 | A1 | 6/2017 | Pande et al. |
| 2019/0110755 | A1 | 4/2019 | Capodilupo et al. |
| 2020/0085314 | A1 | 3/2020 | Romesburg |
| 2021/0052175 | A1 | 2/2021 | Stephens et al. |
| 2023/0233153 | A1 * | 7/2023 | Kwon ..................... A61B 5/26 600/301 |
| 2023/0282352 | A1 * | 9/2023 | Kim ....................... G06Q 50/22 705/2 |

OTHER PUBLICATIONS

Extended European Search Report for European Application No. 21192515.1 dated Feb. 21, 2022, 7 pages.

Lahdenoja et al., "Biomedical Signal Quality Assessment via Learning to Rank with an Application to Mechanical Heart Signals", 2017 Computing in Cardiology (CinC), vol. 44, (Sep. 24-27, 2017), 4 pages.

Markey et al. "Impact of Missing Data in Valuating Artificial Neural Networks Trained on Complete Data", Computers in Biology and Medicine 36.5, (May 2006), pp. 516-525.

Mirza et al., "Conditional Generative Adversarial Nets", arXiv:1411. 1784, (Nov. 6, 2014), 7 pages.

Office Action for European Application No. 21192515.1 dated Oct. 6, 2023, 5 pages.

Office Action for European Application No. 21192515.1 dated Feb. 22, 2024, 7 pages.

* cited by examiner

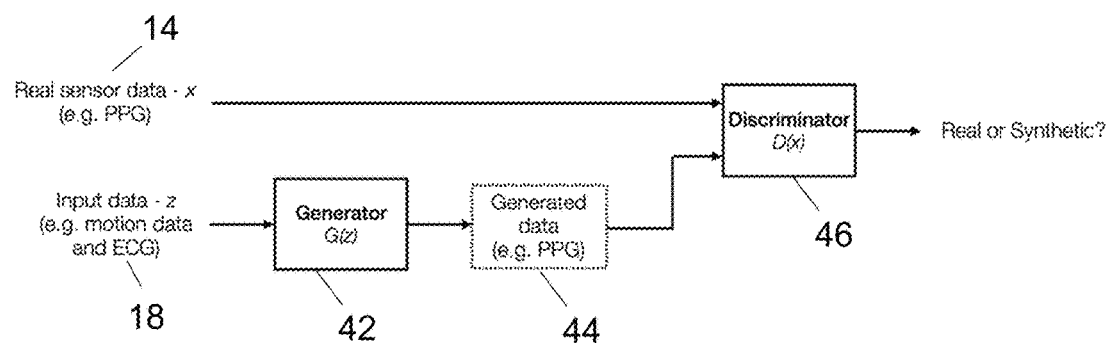
FIG. 9
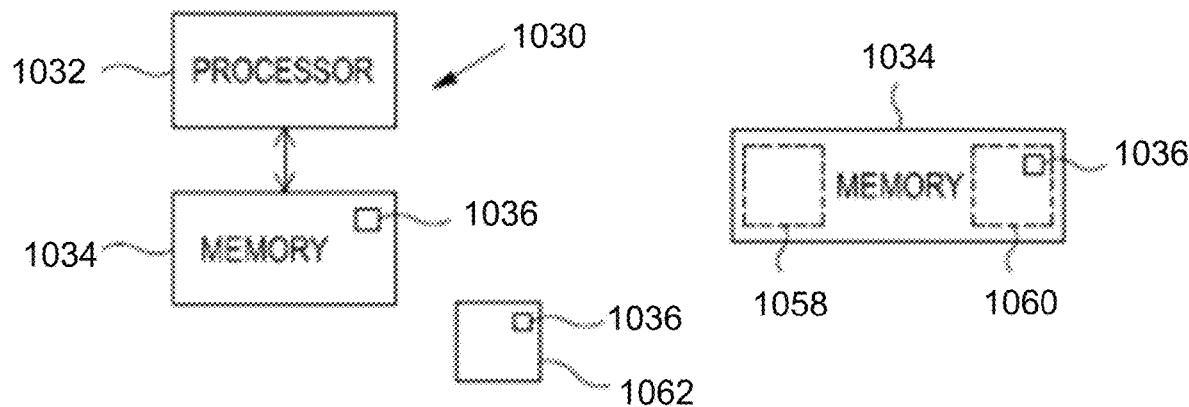
FIG. 10A
FIG. 10B

SENSING

CROSS-REFERENCE TO RELATED APPLICATIONS

This application claims priority to European Patent Application No. 21192515.1, filed Aug. 23, 2021, the entire contents of which are incorporated herein by reference.

TECHNOLOGICAL FIELD

Embodiments of the present disclosure relate to sensing. Some relate to sensing in relation to one or more bio-signals.

BACKGROUND

Some electronic devices, such as some mobile devices and/or some wearable devices, are configured to perform sensing.

For example, some electronic devices are configured to perform sensing in relation to a user to allow, in examples, determination of one or more bio-signals of the user.

It would be desirable to improve sensing by an electronic device.

BRIEF SUMMARY

According to various, but not necessarily all, embodiments there is provided an apparatus comprising means for:
 determining a quality of a data portion of an input sensor data stream based, at least in part, on data of a first data type;
 determining between, at least, generation of two or more streams of a second, different data type including at least one synthesised data stream of the second data type, wherein the determining between generation of two or more streams of a second, different data type is based, at least in part, on the determined quality and wherein the synthesis is based, at least in part, on the data of the first data type; and
 causing generation of at least one stream of the second, different data type based, at least in part, on the determination between generation of two or more streams of the second, different data type.

In some examples, determining between generation of two or more streams of a second, different data type comprises determining between generation of, at least, a filtered data stream of the second data type and a synthesised data stream of the second data type, wherein the filtered data stream is based, at least in part, on the data portion of the input sensor data stream and the synthesised data stream is not based on the data portion of the input sensor data stream.

In some examples, the means are configured to generate a filtered or synthesised data stream of the second data type based, at least in part, on the determination between generation of two or more streams of the second data type, wherein generating a filtered data stream comprises filtering data from the data portion of the input sensor data stream and wherein generating a synthesised data stream comprises generating new data not based on the data portion of the input sensor data stream.

In some examples, the means are configured to:
 replace at least the data portion of the input sensor data stream with a generated stream of the second, different data type.

In some examples, determining the quality of the data portion of an input sensor data stream comprises determining the quality of the data portion of the input sensor data stream based, at least in part, on a corresponding data portion of the first data type.

In some examples, determining the quality of the data portion of an input sensor data stream comprises comparing one or more frequency components of the data portion of the input sensor data stream and the data of the first data type.

In some examples, generation of a synthesised data stream of the second data type is based, at least in part, on at least one of: one or more previous data portions of the input sensor data stream and data from one or more different sensors.

In some examples, the first data type comprises motion data and the second data type comprises biosignal data.

In some examples, the second data type comprises heart rate data and the input sensor data stream is from at least one photoplethysmography sensor.

According to various, but not necessarily all, embodiments there is provided an electronic device comprising an apparatus as described herein and at least one input configured to receive the input sensor data stream.

According to various, but not necessarily all, embodiments there is provided a method comprising:
 determining a quality of a data portion of an input sensor data stream based, at least in part, on data of a first data type;
 determining between, at least, generation of two or more streams of a second, different data type including at least one synthesised data stream of the second data type, wherein the determining between generation of two or more streams of a second, different data type is based, at least in part, on the determined quality and wherein the synthesis is based, at least in part, on the data of the first data type; and
 causing generation of at least one stream of the second, different data type based, at least in part, on the determination between generation of two or more streams of the second, different data type.

In some examples, determining between generation of two or more streams of a second, different data type comprises determining between generation of, at least, a filtered data stream of the second data type and a synthesised data stream of the second data type, wherein the filtered data stream is based, at least in part, on the data portion of the input sensor data stream and the synthesised data stream is not based on the data portion of the input sensor data stream.

In some examples, the method comprises generating a filtered or synthesised data stream of the second data type based, at least in part, on the determination between generation of two or more streams of the second data type, wherein generating a filtered data stream comprises filtering data from the data portion of the input sensor data stream and wherein generating a synthesised data stream comprises generating new data not based on the data portion of the input sensor data stream.

In some examples, the method comprises replacing at least the data portion of the input sensor data stream with a generated stream of the second, different data type.

In some examples, determining the quality of the data portion of an input sensor data stream comprises determining the quality of the data portion of the input sensor data stream based, at least in part, on a corresponding data portion of the first data type.

In some examples, determining the quality of the data portion of an input sensor data stream comprises comparing one or more frequency components of the data portion of the input sensor data stream and the data of the first data type.

In some examples, generation of a synthesised data stream of the second data type is based, at least in part, on at least one of: one or more previous data portions of the input sensor data stream and data from one or more different sensors.

In some examples, the first data type comprises motion data and the second data type comprises biosignal data.

In some examples, the second data type comprises heart rate data and the input sensor data stream is from at least one photoplethysmography sensor.

According to various, but not necessarily all, embodiments there is provided a computer program comprising instructions for causing an apparatus to perform:

determining a quality of a data portion of an input sensor data stream based, at least in part, on data of a first data type;

determining between, at least, generation of two or more streams of a second, different data type including at least one synthesised data stream of the second data type, wherein determining between generation of two or more streams of a second, different data type is based, at least in part, on the determined quality and wherein the synthesis is based, at least in part, on the data of the first data type; and causing generation of at least one stream of the second, different data type based, at least in part, on the determination between generation of two or more streams of the second, different data type.

In some examples, determining between generation of two or more streams of a second, different data type comprises determining between generation of, at least, a filtered data stream of the second data type and a synthesised data stream of the second data type, wherein the filtered data stream is based, at least in part, on the data portion of the input sensor data stream and the synthesised data stream is not based on the data portion of the input sensor data stream.

In some examples, the computer program comprising instructions for causing an apparatus to perform generating a filtered or synthesised data stream of the second data type based, at least in part, on the determination between generation of two or more streams of the second data type, wherein generating a filtered data stream comprises filtering data from the data portion of the input sensor data stream and wherein generating a synthesised data stream comprises generating new data not based on the data portion of the input sensor data stream.

In some examples, the computer program comprising instructions for causing an apparatus to perform:

replacing at least the data portion of the input sensor data stream with a generated stream of the second, different data type.

In some examples, determining the quality of the data portion of an input sensor data stream comprises determining the quality of the data portion of the input sensor data stream based, at least in part, on a corresponding data portion of the first data type.

In some examples, determining the quality of the data portion of an input sensor data stream comprises comparing one or more frequency components of the data portion of the input sensor data stream and the data of the first data type.

In some examples, generation of a synthesised data stream of the second data type is based, at least in part, on at least one of: one or more previous data portions of the input sensor data stream and data from one or more different sensors.

In some examples, the first data type comprises motion data and the second data type comprises biosignal data.

In some examples, the second data type comprises heart rate data and the input sensor data stream is from at least one photoplethysmography sensor.

According to various, but not necessarily all, embodiments there is provided an apparatus comprising at least one processor; and at least one memory including computer program code;

the at least one memory and the computer program code configured to, with the at least one processor, cause the apparatus at least to perform at least a part of one or more methods disclosed herein.

According to various, but not necessarily all, embodiments there is provided an apparatus comprising means for performing at least part of one or more methods disclosed herein.

According to various, but not necessarily all, embodiments there is provided examples as claimed in the appended claims.

The description of a function and/or action should additionally be considered to also disclose any means suitable for performing that function and/or action.

BRIEF DESCRIPTION

Some examples will now be described with reference to the accompanying drawings in which:

FIG. 9 shows another example of the subject matter described herein;

FIG. 10A shows another example of the subject matter described herein; and

FIG. 10B shows another example of the subject matter described herein.

DETAILED DESCRIPTION

Examples of the disclosure relate to apparatus, methods and/or computer programs for and/or involved in sensing.

Some examples of the disclosure relate to apparatus, methods and/or computer programs for improving and/or correcting and/or replacing and/or enhancing bad quality and/or corrupted and/or missing sensor data.

In some, but not necessarily all, examples, the sensor data can be related to and/or indicative of one or more biosignals.

The following description and FIGs describe various examples of an apparatus 10 comprising means for:

determining a quality of a data portion 12 of an input sensor data stream 14 based, at least in part, on data of a first data type 18;

determining between generation of two or more streams of a second, different data type 20 including at least one synthesised data stream 22 of the second data type 20, wherein the determining between generation of two or more streams of a second, different data type is based, at least in part, on the determined quality and wherein synthesis is based, at least in part, on the data of the first data type 18; and causing generation of at least one stream of the second, different data type 20 based, at least in part, on the determination between generation of two or more streams of the second, different data type 20.

Figure 1:
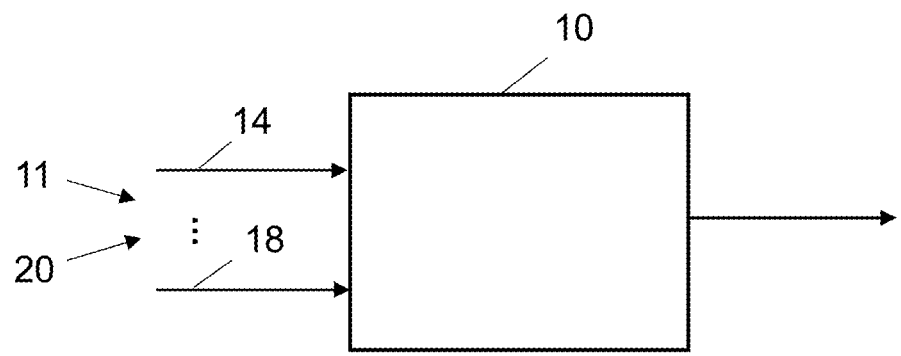
FIG. 1 shows an example of the subject matter described herein.

FIG. 1 schematically illustrates an example of an apparatus 10.

In the example of FIG. 1, the apparatus 10 is configured to receive a plurality of data streams 11, for example from one or more sensors 16 (not illustrated in the example of FIG. 1) including at least one data stream 11 that can be considered an input sensor data stream 14 and at least one data stream 11 of a first data type 18.

In examples, the apparatus 10 can be a standalone apparatus. Accordingly, in examples, the apparatus 10 is not comprised and/or integrated in an electronic device.

In examples, the apparatus 10 does not receive and/or transmit information to one or more different, separate apparatus/devices when performing one or more methods described herein.

In examples, the apparatus 10 can be comprised and/or integrated in an electronic device. For example, the apparatus 10 can be comprised in and/or integrated with one or more sensors.

The data stream 11 of a first data type 18 can be considered data of a first data type 18.

The input sensor data stream 14 can be considered a data stream 11 of a second, different data type 20.

In examples, the first data type 18 can comprise motion data and the second, different data type 20 can comprise photoplethysmography data.

In examples, the plurality of data streams 11 comprise one or more data portions 12. For example, the input data stream 14 can comprise one or more data portions 12 and the data of the first data type 18 can comprise one or more corresponding data portions 12.

In examples, a data portion 12 can be considered data within a window taken from a data stream 11.

In examples, the apparatus 10 is configured to determine one or more data portions 12 from the input data streams 11. In examples, the apparatus 10 is configured to split and/or section and/or portion one or more of the input data streams 11 into one or more data portions 12.

The apparatus 10 is configured to determine a quality of a data portion 12 of the input sensor data stream 14 and, based at least in part on the determined quality, to determine between, at least, generation of two or more streams of a second, different data type 20 including at least one synthesised data stream 22 of the second data type 20.

As used herein, the term "determining" (and grammatical variants thereof) can include, not least: calculating, computing, processing, deriving, investigating, looking up (for example, looking up in a table, a database or another data structure), ascertaining and the like. Also, "determining" can include receiving (for example, receiving information), accessing (for example, accessing data in a memory) and the like. Also, "determining" can include resolving, selecting, choosing, establishing, and the like.

In examples, the apparatus 10 is configured to determine between, at least, filtering data and synthesising data.

In the example of FIG. 1, the apparatus 10 is configured to cause generation of at least one stream of the second, different data type 20 based, at least in part, on the determination between generation of two or more streams of the second, different data type 20.

In examples, the apparatus 10 is configured to transmit one or more signals to cause generation of at least one stream of the second, different data type 20.

In examples, the apparatus 10 is configured to generate the at least one stream of the second, different data type. For example, the apparatus is, in examples, configured to, at least, filter the data portion 12 and/or to synthesise data to generate at least one stream of the second, different data type 20.

Accordingly, in examples, the apparatus 10 is configured to output the generated at least one stream of the second, different data type 20.

In examples, the apparatus 10 is configured to replace the data portion 12 of the input sensor data stream 14 with the generated at least one stream of the second, different data type 20.

Accordingly, in examples, the apparatus 10 is configured to output a modified version of the input sensor data stream 14 comprising the generated at least one stream of the second different data type 20.

In examples, the apparatus 10 is configured to generate the modified version of the input sensor data stream 14 and to use the modified version of the input sensor data stream 14 in one or more determinations.

In examples, the apparatus 10 can comprise any number of additional elements not illustrated in the example of FIG. 1.

Figure 2:
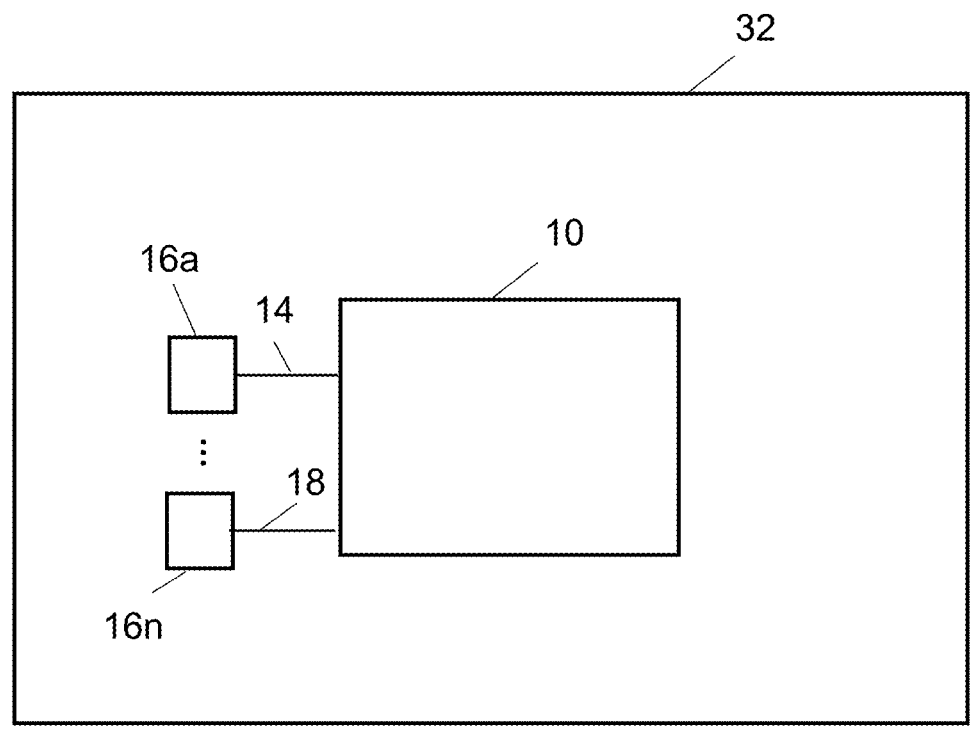
FIG. 2 shows another example of the subject matter described herein.

FIG. 2 schematically illustrates an example of an electronic device 32.

In the illustrated example, the electronic device 32 comprises a plurality of sensors 16a to 16n and an apparatus 10 as described in relation to FIG. 1.

The electronic device 32 can be and/or comprise any suitable electronic device 32. For example, the electronic device 32 can be and/or comprise any suitable sensing device.

In examples, the electronic device 32 can be and/or comprise any suitable electronic device for use in determining one or more bio-signals of a user.

In examples, the electronic device 32 can be and/or comprise any suitable personal device, and/or any suitable mobile device, and/or any suitable wearable device and so on. For example, electronic device 32 can be and/or comprise a smart watch, a smart ring, a smart ear worn device, smart glasses and so on.

In examples, the electronic device 32 can be considered an apparatus.

The electronic device 32 can comprise any suitable number of sensors 16a to 16n.

In examples, the sensors 16a to 16n can be and/or comprise any suitable sensors 16a to 16n. For example, the sensors 16a to 16n can comprise: one or more inertial measurement units, one or more photoplethysmography (PPG) sensors, one or more galvanic skin response (GSR) sensors, one or more electrocardiogram (ECG) sensors, one or more electroencephalogram sensors and/or one or more microphones and so on.

In the example of FIG. 2 the apparatus 10 is configured to receive an input sensor data stream 14 from a first sensor 16a and data of a first data type 18 from a second sensor 16b.

In examples, the electronic device 32 can comprise any number of additional elements not illustrated in the example of FIG. 2. For example, the electronic device 32 can comprise one or more transceivers and/or one or more user interfaces and/or one or more displays and so on.

Additionally, or alternatively, one or more elements of the electronic apparatus 32 illustrated in the example of FIG. 2 can be integrated and/or combined. For example, two or more of the sensors 16a to 16n can be integrated and/or combined.

Additionally, or alternatively, the apparatus 10 can be integrated and/or combined with one or more sensors 16.

As illustrated in the example of FIG. 2, the sensors 16a to 16n are and/or can be considered to be operationally coupled to the apparatus 10 and any number or combination of intervening elements can exist between them (including no intervening elements).

In examples, the electronic device 32 can comprise at least one input configured to receive data from one or more sensors 16 to 16n.

Accordingly, in examples, FIG. 2 illustrates an electronic device 32 comprising an apparatus 10 as described herein and at least one input configured to receive the input sensor data stream 14.

Figure 3:
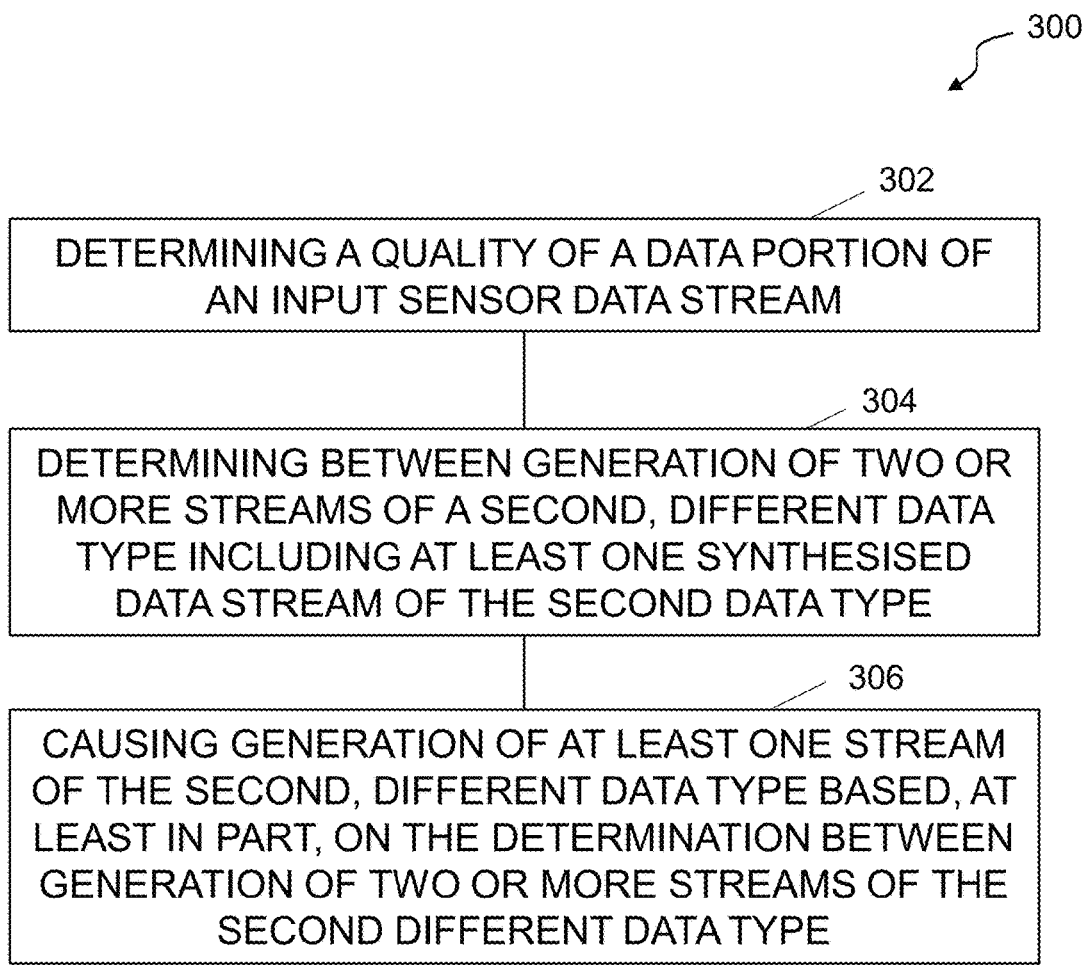
FIG. 3 shows another example of the subject matter described herein.

FIG. 3 illustrates an example of a method 300.

One or more of the features discussed in relation to FIG. 3 can be found in one or more of the other FIGs. During discussion of FIG. 3, reference will be made to other FIGs for the purposes of explanation.

In examples, method 300 can be considered a method of sensing.

In examples, method 300 can be considered a method of enabling sensor data enhancement and/or improvement.

In examples, method 300 can be considered a method of enhancing and/or improving and/or fixing sensor data.

In examples, method 300 can be considered a method of enabling improved accuracy in one or more measurements.

In examples, method 300 can be considered a method of enabling improved accuracy in one or more measurements.

In examples, method 300 can be performed by any suitable apparatus comprising any suitable means for performing the method 300.

In examples, method 300 can be performed by the apparatus of FIGS. 10A and 10B and/or the apparatus of FIG. 1.

Some, but not necessarily all, examples involve the use of data of different data types.

In examples, a data type can be considered to be data from a type of sensor 16. For example, data from a first type of sensor 16 can be considered data of a first data type and data from a second, different type sensor 16 can be considered data of a second, different data type.

In examples, a type of sensor 16 can be considered a sensor 16 comprising hardware configured to determine one or more types of data/information.

In examples, a type of sensor 16 can be considered a sensor 16 that is configured to determine one or more types of information using one or more methods and/or technologies.

For example, a photoplethysmography sensor can be considered a first type of sensor, and an electrocardiogram sensor can be considered a second type of sensor.

Accordingly, in examples, data from a photoplethysmography sensor can be considered a first type of data and data from an electrocardiogram sensor can be considered a second, different type of data.

In examples, a data type can be considered to be data indicative of one or more parameters and/or attributes to be measured. In examples, a data type can be considered to be data indicative of one or more physical parameters and/or attributes to be measured. For example, data indicative of heart rate can be considered a first data type and data indicative of motion can be considered a second, different data type.

Accordingly, data from two different sensors 16 that both provide data of a common physical attribute can be considered data of the same type. For example, heartrate data from a photoplethysmography sensor and an electrocardiogram sensor can both be considered data of a first type.

In examples, data can be indicative of multiple parameters and/or attributes and therefore can, in examples, be considered to be of and/or comprise multiple data types.

At block 302 method 300 comprises determining a quality of a data portion 12 of an input sensor data stream 14 based, at least in part, on data of a first data type 18.

In examples, determining a quality of a data portion 12 of an input sensor data stream 14, based at least in part, on data of a first data type 18 can be performed in any suitable way using any suitable method.

For example, the data of the first data type 18 can be used in any suitable way in determining the quality of the data portion 12.

In examples, determining the quality of the data portion 12 comprises determining the suitability of the data of the data portion 12 for use in one or more downstream determinations and/or for use by one or more downstream applications.

In examples, determining the quality of the data portion 12 comprises determining an amount and/or a level of corrupted and/or bad and/or missing data and/or determining an amount of noise and so on.

In examples, determining the quality of the data portion 12 comprises analysing data of the data portion 12 in combination with, at least, the data of the first data type 18.

In examples, determining the quality of the data portion 12 comprises comparing the data of the data portion 12 and/or data determined from the data of the data portion 12 with and/or against, at least, the data of the first data type 18 and/or data determined from the data of the first data type 18.

In examples, determining the quality of the data portion 12 comprises determining a correlation between the data of the data portion 12 and, at least, the data of the first data type 18.

In examples, determining the quality of the data portion 12 comprises performing a spectral analysis of the data of the data portion 12 and/or the data of the first data type 18.

In examples, performing a spectral analysis comprises determining one or more frequency components 28.

In examples, determining the quality of the data portion 12 comprises determining one or more metrics of the data of the data portion 12 and/or the data of the first data type 18.

In examples, the one or more metrics can be sensor specific and can be determined separately for different sensors.

In examples, the one or more metrics are determined from the time domain, frequency domain and/or with template matching.

In examples, the one or more metrics are determined, at least in part, from the morphology of the signal.

Examples of metrics for a PPG sensor include, but are not limited to: perfusion index, systolic phase duration/rise time, ratio of systolic to diastolic phase, pulse wave duration, pulse wave amplitude, skewness, kurtosis, frequency domain kurtosis, pearson correlation of template matching and so on.

Examples of metrics for an ECG sensor include, but are not limited to: flat line detection, baseline wander, skewness, kurtosis, R-R interval variability, pearson correlation of template matching and so on.

Examples of metrics for motion data include, but are not limited to: time-domain features such as mean and root mean square, and frequency-domain features such as DC component and information entropy.

Accordingly, in examples, determining the quality of the data portion 12 of an input sensor data stream 14 comprises comparing one or more frequency components 28 of the data portion 12 of the input sensor data stream 14 and the data of the first data type 18. See, for example, FIG. 4.

Any suitable input sensor data stream 14 can be used. For example, any suitable input data from any suitable sensor or sensors 16 can be used as and/or considered an input sensor data stream 14.

For example, data from one or more sensors 16 discussed in relation to FIG. 2 can be used.

In examples, the input sensor data stream 14 can be considered an input data stream 11 of a second, different data type 20.

In examples, the second, different data type 20 can comprise any suitable data type.

In examples, the second data type 20 can comprise data from one or more sensors 16 configured to allow determination of one or more bio-signals of a person and/or user of an apparatus. In examples, data of the second data type 20 can be considered bio-signal data.

In examples, the data of the second data type 20 can be indicative of one or more bio-signals of a person and/or user of an apparatus. In examples, a bio-signal can be considered a measurement of one or more physical and/or mental parameters and/or attributes and/or characteristics of a person.

Any suitable bio-signal or signals can be used. For example, heart rate, heart rate variability, respiration rate, blood oxygen saturation, skin conductance and/or body-core temperature and so on.

Any suitable portion of the input sensor data stream 14 can be used as and/or considered a data portion 12 of the input sensor data stream 14. For example, a portion of any suitable duration can be used as and/or considered a data portion 12 of the input sensor data stream 14.

In examples the input sensor data stream 14 is split into a number of portions.

In examples, the input sensor data stream 14 is windowed following an overlapping-sliding-window approach resulting in time-dependent portions of data.

Accordingly, in examples method 300 comprises splitting the input sensor data stream 14 into a number of portions.

In examples, method 300 comprises spitting a plurality of input data streams 11 into a number of portions.

In examples, the data portion 12 can have any suitable time duration. For example, the data portion 12 can have a duration in the range 5 seconds to 60 seconds. For example, the data portion 12 can have a duration in the range 10 seconds to 30 seconds.

In examples, the time duration of the data portion 12 is dependent on the data being measured. For example, the duration of the data portion 12 can be dependent on a physical parameter, such as heart rate, that is to be determined.

In examples, the duration of the data portion 12 can be dependent on the sampling frequency used.

In examples, the data of the first data type 18 comprises any suitable data. For example, the data of the first data type 18 can comprise data from any suitable sensor 16 or sensors 16, such as one or more sensors 16 discussed in relation to FIG. 2.

Accordingly, in examples, the data of the first data type 18 can comprise a data stream 11 of the first data type 18.

In examples, the first data type 18 can comprise any suitable data type.

In examples, the first data type can comprise any suitable data correlated in any suitable way with the data and/or data type of the input sensor data stream 14.

In examples, the data of the first data type 18 is correlated with noise and/or artefacts affecting the quality of the data portion 12 of the input sensor data stream and also correlated with data portion 12 itself such that, for example, the data of the first data type 12 can be used in synthesis of data for the data portion 12.

For example, motion data of a person can be considered to be correlated with noise introduced into one or more bio-signals of the person and also with one or more bio-signals of a person as motion of a person can affect readings from one or more sensors 16 and also can cause a change in one or more bio-signals of the person.

Similarly, one or more bio-signals of a person can be considered to be correlated with one or more different bio-signals of the person.

In general, data of a first type, such as motion data can be useful to determine the quality of another sensor whenever motion, for example, induces changes to the readings of the other sensor which are correlated with the motion itself.

In examples involving biosensors in contact with the skin (for example PPG and ECG), motion results in the displacement of the sensor over the skin or movement of the tissues underneath the senor. This causes biosensor's readings that are synchronised with the readings from the motion sensor.

As an example, if a person runs and swings their arm with a certain frequency X (for example, 5 Hz), the watch on their wrist will oscillate at the same (or very similar frequency) producing motion artefacts on the PPG signal at a similar frequency.

By doing a spectral analysis (for example., FFT) high energy at the frequency X for both motion and PPG signals would be seen. Notably, the PPG signal had a much lower energy at that frequency before the motion started because the typical range for heart rate is much lower than that (typically in the range 0.8 Hz-3.5 Hz).

The similarity in frequency content between motion and PPG signal and the fact that the PPG signal did not have that frequency component previously, is a clear indication that the PPG signal is being affected by the motion. In general, the higher the energy at frequency X observable in the PPG signal the higher the level of corruption (that is, the lower the quality of the signal).

In examples, in the context of biosensors, motion data has the additional utility of helping with the generation of synthetic data because motion from physical activity induces physiological changes in the body (for example, increased heart rate or decreased heart rate variability).

Hence, even if the raw bio-signal is corrupted by noise, knowing the motion status of the user can be used to help producing clean data. In examples this is done by letting a GAN learn the mapping between motion and raw bio-signals, see, for example, FIG. 6.

In examples, motion data can be useful in generating clean PPG data when there is a periodic motion that is likely to affect the PPG data, for example when walking, running or cycling.

Similarly, for PPG sensors embedded in smart earbuds, motion data can help when the user is speaking or chewing. In such examples there might not be a change in the physiological response of the body but the motion data will still be useful to determine the level of noise in the PPG data and generate clean data.

In examples, the first data type 18 can comprise data from a motion sensor, such as an inertial measurement unit.

In examples, the data of the first data type 18 can be indicative of motion of a person and/or user of an apparatus.

Accordingly, in examples, the first data type 18 comprises motion data and the second data type 20 comprises bio-signal data.

In examples, motion data of a person can be considered to comprise bio-signal data. Accordingly, in examples, the first data type 18 comprises motion data and the second data type 20 comprises different bio-signal data.

In examples, different bio-signal data can be considered bio-signal data that is not motion data.

In examples, the second data type 20 comprises information of one or more physical parameters of a person and the first data type 18 comprises information of movement of a device worn by the person.

In examples, the second data type 20 comprises physiological information and the first data type 18 comprises non-physiological information.

In examples the data of the first data type 18 is split into a number of portions, for example into windows. In examples, this can be done in any suitable way using any suitable method.

In examples, the data of the first data type 18 is split into a number of portions, for example windows, in a similar way and/or the same way as the input sensor data stream 14.

In examples, determining the quality of the data portion 12 of an input sensor data stream 14 comprises determining the quality of the data portion 12 of the input sensor data stream 14 based, at least in part, on a corresponding data portion of the first data type 18.

In examples, a data portion of the first data type 18 that corresponds with the data portion 12 of the input sensor data stream 14 in any suitable way can be used.

In examples, a corresponding data portion can be considered a linked and/or parallel and/or matching data portion and so on.

In examples, a data portion of the first data type 18 that corresponds temporally, at least partially, with the data portion 12 of the input sensor data stream 14 can be used.

For example, a data portion of the first data type 18 that at least partially temporally overlaps with the data portion 12 of the input sensor data stream 14 can be used. See, for example, FIG. 4.

In examples, data from any suitable number of sensors 16 of any suitable type or types can be used in determining the quality of the data portion 12 of the input sensor data stream 14. For example, data from a sensor 16 of a third, different data type and/or data from a sensor 16 of a fourth, different data type can be used in the determination and so on.

Accordingly, in examples, method 300 comprises and/or can be considered to comprise receiving data from a plurality of sensors 16.

In examples, data from any suitable number of sensors 16 is split into a number of portions in a similar way and/or the same way as the input sensor data stream 14 and/or data of the first data type 18.

Figure 4:
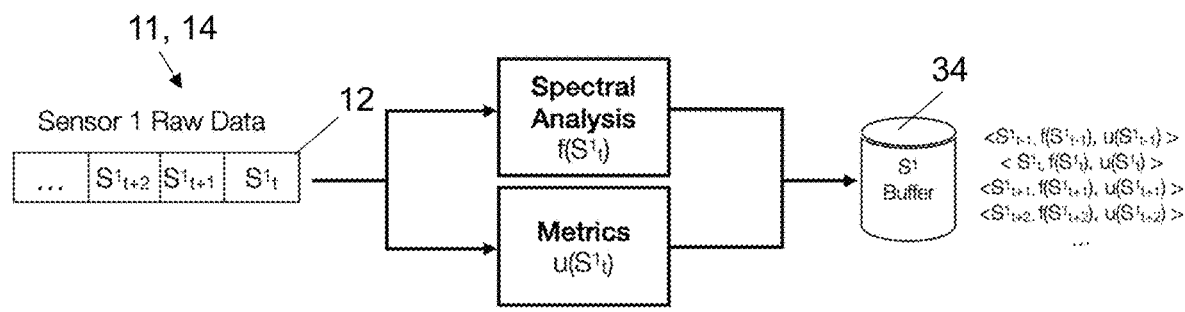
FIG. 4 shows another example of the subject matter described herein.

Reference is made to FIG. 4.

FIG. 4 illustrates an example of a method that can be used in determining a quality of a data portion 12 of an input sensor data stream 18.

The example of FIG. 4 depicts pipelines for two input data streams 11. However, in examples pipelines for any suitable number of input data streams 11 can be used.

In examples, motion data can be considered to be separate from data from other sensors 16, which can be considered sensor data.

In the example of FIG. 4 the upper pipeline is for an input sensor data stream 14, from a first sensor 16 and the lower pipeline is for data of the first data type 18. In the illustrated example, first data type is motion data of a person, from a motion sensor.

The stream of raw data coming from each sensor $S^x$ is windowed following an overlapping-sliding-window approach resulting in time-dependent portions 12 of data denoted with $S^x_t$ in FIG. 4.

In the example of FIG. 4, for each of these portions 12 a spectral analysis, $f(S^x_t)$, is performed to determine the signal constituent frequencies and metrics are determined that can be used to determine the quality of the input sensor data stream 14 and the correlation between different sensors 16.

In the example of FIG. 4, the resulting frequencies and metrics are stored alongside the original signal portion 12 and/or window in a temporary buffer 34 for each sensor 16. When data from any of these sensors 16 is missing, the relative window slot in the buffer 34 is filled with NULL to indicate that data was missing for that window.

In FIG. 4, the buffer 34 holds data for a limited number of windows to avoid excessive use of memory.

In examples the buffers 34 are maintained aligned in the sense that for each window t there is an entry in all buffers 34. Aligned data portions 12 and/or windows can be considered corresponding data portions 12 and/or windows.

The pipelines in the example of FIG. 4 are similar, however the metrics in different pipelines can differ. For example, the metrics computed by the function $s(M_t)$ for the motion data can be different than the metrics computed for other sensors 16, for example sensors used for bio-signals, and the results can be stored in a different buffer 34.

In examples, data from the sensor buffers 34 and from the motion buffer 34, is read one window at the time, and based, at least in part, on the determined metrics the quality of the data portions 12 of the input sensor data stream can be determined.

Referring again to FIG. 3. At block 304, method 300 comprises determining between, at least, generation of two or more streams of a second, different data type 20 including at least one synthesised data stream 22 of the second data type 20, wherein the determining between generation of two or more streams of a second, different data type 20 is based, at least in part, on the determined quality and wherein the synthesis is based, at least in part, on the data of the first data type 18.

In examples, determining between, at least, generation of two or more streams of a second, different data type 20, including at least one synthesised data stream 22 can be performed in any suitable way using any suitable method.

In examples, determining between, at least, generation of two or more streams of a second, different data type 20 comprises determining if the determined quality of the data portion 12 of the input sensor data stream 14 is sufficient for use in one or more downstream determinations and/or one or more downstream applications.

For example, determining if the determined quality of the data portion 12 of the input sensor data stream 14 is sufficient for use in determining one or more bio-signals of a person.

In examples, determining between, at least, generation of two or more streams of a second, different data type 20 comprises analysing and/or comparing and/or considering and/or evaluating the determined quality of the of the data portion 12 of the input sensor data 14 against one or more thresholds.

In examples, determining between, at least, generation of two or more streams of a second, different data type 20 comprises analysing and/or comparing and/or considering and/or evaluating a determined amount and/or a level of noise and/or corrupted and/or bad and/or missing data against one or more thresholds.

In examples, determining between, at least, generation of two or more streams of a second, different data type 20 comprises analysing and/or considering and/or evaluating one or more frequency components and/or metrics of the data portion 12 of the input sensor data stream 14 and/or the data of the first data type 18.

In examples, determining between, at least, generation of two or more streams of a second, different data type 20 comprises comparing one or more metrics to one or more thresholds.

For example, for systolic phase duration/rise time, permitted values for good quality data can be in the range 0.08 to 0.49.

For example, for the ratio of systolic to diastolic phase an upper limit for good quality data can be 1.1 and so on.

In examples, determining between, at least, generation of two or more streams of a second, different data type 20 comprises determining, based at least in part on the determined quality, if the data portion 12 of the input sensor data stream 14 can be cleaned and/or enhanced and/or filtered to sufficiently improve the quality of the data portion 12 of the input sensor data stream 14 for use in one or more downstream determinations and/or for use by one or more downstream applications.

For example, when the data portion 12 of the input sensor data stream 14 is mildly affected by noise or artifacts, generation of a cleaned and/or enhanced, for example filtered, stream of the second data type 20 can be determined.

If it is determined that the quality of the data portion 12 of the input sensor data stream 14 is such that the data portion 12 can be cleaned and/or enhanced and/or filtered to sufficiently improve the quality for use in one or more downstream determinations and/or for use by one or more downstream applications, generation of a non-synthesised data stream of the second data type 20 can be determined.

If it is determined that the quality of the data portion 12 of the input sensor data stream 14 is such that the data portion 12 cannot be cleaned and/or enhanced and/or filtered to sufficiently improve the quality for use in one or more downstream determinations and/or for use by one or more downstream applications, generation of a synthesised data stream 22 of the second data type 20 can be determined.

For example, if the data portion 12 is significantly corrupted and/or comprises a large amount of noise and/or is missing, generation of a synthesised data stream 22 of the second data type 20 can be determined.

In examples, movement of a person, such as a user of an electronic device 32, can induce quality issues in the data of the input sensor data stream 14.

In examples, if noise induced by the user's motion on one or more sensors 16 has frequency components that are outside of the typical frequencies of the raw sensor data, then filtering can be employed to remove noise frequencies while preserving the underlying frequency or frequencies, for example heart rate.

If, however, the noise has frequency components that, at least, overlap with the ones of the signals, such as bio-signals, making filtering difficult or impossible, or if raw sensor data is completely missing, data synthesis can be employed.

In examples, block 304 can comprise determining between generation of any suitable number of streams of a second, different data type 20.

Accordingly, in examples, block 304 can comprise determining between generation of any suitable number of streams of a second, different data type 20.

In examples, block 304 can comprise determining between two or more generation techniques and/or methods of a stream of a second, different data type 20 including at least one synthesis technique and/or method.

For example, block 304 can comprise determining between, at least, generation of a filtered stream 24 of a second, different data type 20 and generation of a synthesised stream 22 of a second, different data type 20.

In examples, a filtered data stream 24 is based, at least in part, on the data portion 12 of the input sensor data stream 14 and the synthesised data stream 22 is not based on the data portion 12 of the input sensor data stream 14.

Accordingly, in examples, determining between generation of two or more streams of a second, different data type 20 comprises determining between generation of, at least, a filtered data stream 24 of the second data type and a synthesised data stream 22 of the second data type 20, wherein the filtered data stream 24 is based, at least in part, on the data portion 12 of the input sensor data stream 14 and the synthesised data stream 22 is not based on the data portion 12 of the input sensor data stream 14.

In examples, a filtered data stream 24 can be considered to be and/or comprise a subset of the data of the data portion 12 of the input sensor data stream 14.

In examples, a synthesised data stream 22 can be considered not to be and/or not to comprise a subset of the data of the data portion 12 of the input sensor data stream 14.

In examples, generation of a synthesised data stream 22 of the second data type 20 is based, at least in part, on the data of the first data type 18.

Accordingly, in examples, determination of the quality of the data portion 12 of the input sensor data stream 14 and generation of synthesised data stream of the second data type 20 are both based, at least in part, on the data of the first data type 18.

In examples, both the quality of the data portion 12 and the data of the data portion 12 correlate, in some way, with the data of the first data type 18.

In examples, a filtered data stream 24 and/or a synthesised data stream 22 can be based, at least in part, on data from one or more other data streams 11, for example, data from one or more other sensors 16.

In examples, the two or more streams of a second, different data type 20 can be considered two or more data portions 12 of the second, different data type 20.

In examples, the two or more streams of a second, different data type 20 are configured to match the data type of the data portion 12 of input sensor data stream 14.

In examples the second data type 20 comprises heart rate data and the input sensor data stream 14 is from at least one photoplethysmography (PPG) sensor.

In examples, PPG comprises more than just heart rate data. For example, changes in amplitude and/or shape of a PPG signal, as opposed to its frequency, can provide biosignal and/or medically relevant information.

In examples, it is determined based, at least in part, on the determined quality not to generate a stream of a second, different data type 20.

For example, if it is determined that the quality of the data portion 12 of the input sensor data stream 14 is sufficient for use in one or more downstream determinations and/or for use by one or more downstream applications, the data portion 12 can remain unchanged, in which case block 306 would not be performed for such a data portion 12.

Figure 5:
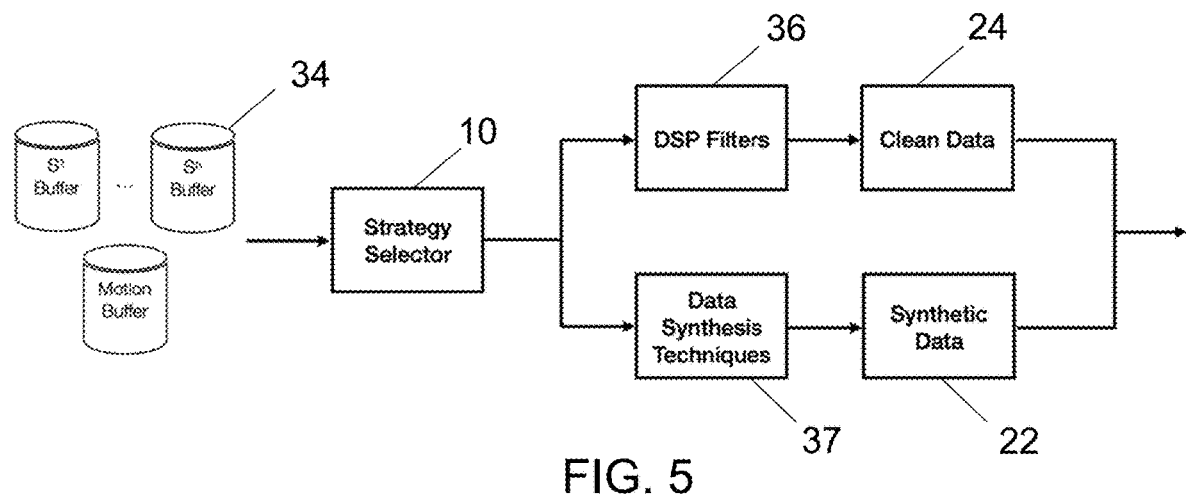
FIG. 5 shows another example of the subject matter described herein.

Reference is made to FIG. 5.

FIG. 5 illustrates an example of a method that can be used in determining, at least, generation of two or more streams of a second, different data type 20. Reference is also made to FIG. 4 and the corresponding description.

In the example of FIG. 5, an apparatus 10, for example the apparatus 10 of FIG. 1, reads data from the sensor buffers 34 and from the motion buffer, one window at a time, see the example of FIG. 4.

Based on the computed metrics, the apparatus 10 decides (and in examples applies) the best strategy to adopt in order to improve the quality of the sensor readings affected by noise or that are missing.

In the example of FIG. 5, the apparatus 10 selects between two main strategies which correspond to different levels of data corruption.

When sensor data is mildly affected by noise or motion artifacts, the apparatus can select the first strategy, which uses digital signal processing (DSP) filters 36 both in the time and frequency domain. These include, but are not limited to, low-pass, high pass filters, band-pass, notch filters and/or adaptive filters.

When raw sensor data is irrecoverable or completely missing the second strategy using data synthesis technique(s) 37 will be selected since it uses techniques that can synthesise new data.

In the example of FIG. 5 the apparatus 10 uses the computed metrics to select either appropriate DSP filter(s) 36 to filter the data or generative technique(s) 37 to synthesise new data.

Referring again to FIG. 3. At block 306, method 300 comprises causing generation of at least one stream of the second, different data type 20 based, at least in part, on the determination between generation of two or more streams of the second, different data type 20.

Consequently, FIG. 3 illustrates a method 300 comprising:
determining a quality of a data portion 12 of an input sensor data stream 14 based, at least in part, on data of a first data type 18;
determining between, at least, generation of two or more streams of a second, different data type 20 including at least one synthesised data stream 22 of the second data type, wherein the determining between generation of two or more streams of a second, different data type 20 is based, at least in part, on the determined quality and wherein the synthesis is based, at least in part, on the data of the first data type 18; and
causing generation of at least one stream of the second, different data type 20 based, at least in part, on the determination between generation of two or more streams of the second, different data type 20.

In examples, block 306 can be considered to comprise causing generation of at least one stream of the second, different data type determined at block 304.

In examples, causing generation of at least one stream of the second, different data type 20 can be considered controlling generation of and/or determining to generate at least one stream of the second, different data type 20.

In examples, causing generation of at least one stream of the second, different data type 20, based at least in part, on the determination between generation of two or more streams of the second, different data type 20 can be performed in any suitable way using any suitable method.

In examples, causing generation at block 306 comprises transmitting one or more signals and/or one or more messages comprising information. For example, causing generation at block 306 can comprise transmitting one or more signals comprising information to cause and/or control an apparatus to perform the generation.

Accordingly, in examples, block 306 and the generation of the at least one stream of the second, different data type can be performed by different apparatus 10 and/or electronic devices 32.

In examples, block 306 and the generation of the at least one stream of the second, different data type can be performed by a single apparatus 10 and/or electronic device 32.

Accordingly, in some, but not necessarily all, examples, method 300 comprises generating at least one stream of the second, different data type 20 based, at least in part, on the determination between generation of two or more streams of the second, different data type 20.

In examples, method 300 comprises causing generation of and/or generating a filtered 24 or synthesised data stream 22 of the second data type 20 based, at least in part, on the determination between generation of two or more streams of the second data type 20, wherein generating a filtered data stream 24 comprises filtering data from the data portion 12 of the input sensor data stream 14 and wherein generating a synthesised data stream 22 comprises generating new data not based on the data portion 12 of the input sensor data stream 14.

In examples, generating a filtered data stream 24 of the second data type 20 can be performed in any suitable way, using any suitable method. For example, one or more DSP filters can be used, as discussed in relation to block 304.

In examples, generating a synthesised data stream 22 of the second data type 20 can be performed in any suitable way, using any suitable method. For example, any suitable generative method or methods can be used.

In examples, generation of a synthesised data stream 22 of the second data type 20 is based, at least in part, on at least one of: one or more previous data portions 12 of the input sensor data stream 14 and data from one or more different sensors 30.

Accordingly, in examples, generation of a synthesised data stream 22 of the second data type is based, at least in part, on the data of the first data type 18 and at least one of: one or more previous data portions 12 of the input sensor data stream 14 and data from one or more different sensors 30.

In examples, the one or more different sensors 30 comprise one or more different sensors 30 correlated with the input sensor data stream 14.

In examples, generating a synthesised data stream 22 of the second data type 20 comprises using one or more neural networks. Any suitable neural network or networks can be used.

In examples, generating a synthesised data stream 22 of the second data type 20 comprises using one or more conditional generative adversarial nets (CGANs) 38.

Figure 6:
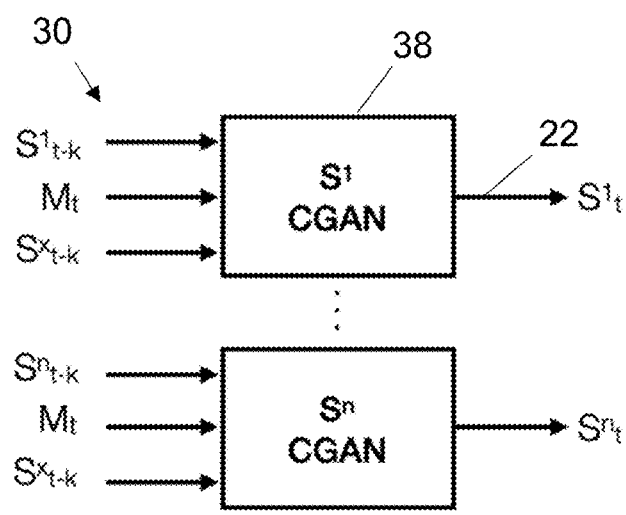
FIG. 6 shows another example of the subject matter described herein.

Reference is made to FIG. 6.

FIG. 6 illustrates an example of use of CGANs 38. FIG. 6 is described in relation to sensors and data related to bio-signals, however in examples any suitable sensors and data types can be used.

In the example of FIG. 6 The use of CGANs 38 allows the generation of synthetic sensor data 22 to be conditioned based on a combination of the following inputs:

previous windows of the same sensor 16 (that is, historical data), for example previous data portions 12 of the input sensor data stream 14;

data 30 from one or more correlated sensors 16 (For example, ECG to generate PPG and vice versa);

motion sensor data. In examples, motion sensor data can be considered data of the first data type 18

With the historical data the CGAN 38 exploits the fact that bio-signals are typically slow changing.

For example, if a PPG sensor to measure heart rate is considered, even if the raw signal is immediately affected by motion when the user starts running, the actual heart rate of the user does not change significantly the moment the user starts running, but it takes some time to increase. Hence the CGAN 38 can, at least initially, rely on PPG data collected before the motion started to generate synthetic data during the motion.

With the data from the correlated sensor(s) the correlations that exists between certain sensors 16 can be captured and sensors 16 that are less affected by noise can be exploited to improve the raw streams of other sensors.

Figure 8:
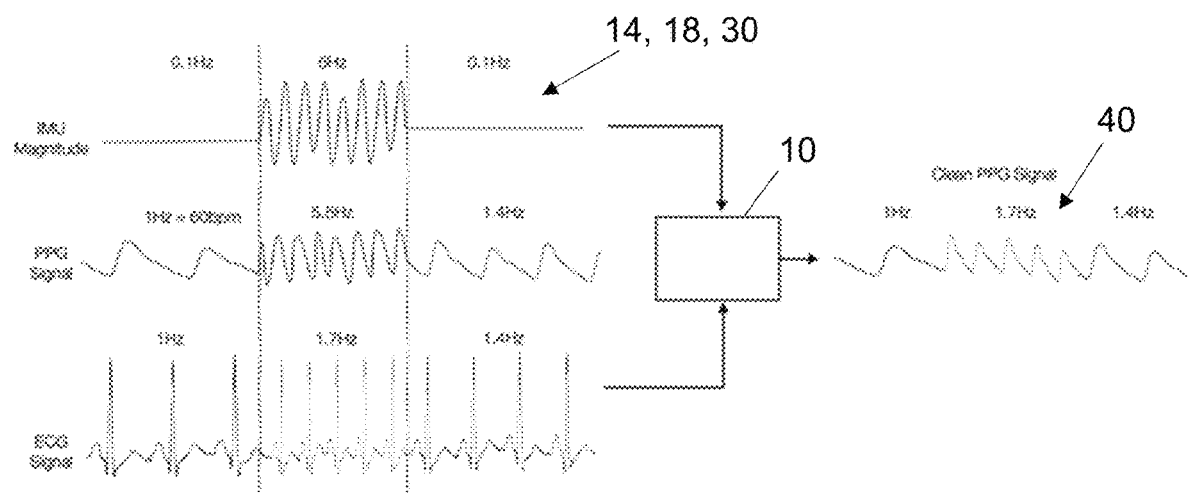
FIG. 8 shows another example of the subject matter described herein.

For example, in a scenario where PPG and ECG measure the underlying user's heart rate but only the PPG is heavily affected by noise (see, for example, FIG. 8).

In this case the CGAN 38 could incorporate the ECG signal in order to synthesise PPG data while the user is moving.

In examples, the apparatus 10 determine which sensors are more or less affected by noise in order to take advantage of these correlations.

In the worst-case scenario, there will be no other correlated sensors 16 that can be used for this purpose because they are also heavily affected by motion or missing. In this case the apparatus 10 can still, for example, rely on the motion sensor data and on previous data to synthesise sensor readings for the input sensor data stream 14 from the target sensor(s).

The motion sensor data is used, in examples, to capture the dynamics of how bio-signals change in response to changes in the user's motions status (for example, the heart rate increases when the user is running) and condition the generation of synthesised data 22 based on the current motion data.

As mentioned earlier, when, for example, PPG data is heavily affected by motion artifacts, the CGAN 38 can initially rely on previous PPG data. However, if the user keeps moving the CGAN 38 can incorporate knowledge about how the bio-signals are affected by motion in order to synthesise more accurate sensor data for the input sensor data stream 14.

In examples, a separate CGAN model 38 is employed for each sensor 16 that might be affected by noise or missing, as can be seen by CGAN1 to CGANn in the example of FIG. 6.

For instance, for sensor S1 (for example, PPG), providing an input sensor data stream 14 there will be an S1 CGAN model 38 which, for each time window t takes in input: previous windows of the same sensor (S1t−k), motion data at the current time window/data portion (Mt) and other sensor data at previous time windows/data portions (Sxt−k). The output of such model is the synthetic data 22 for sensor at the current time window (S1t)/data portion.

In examples, training of a neural network, such as a CGAN 38, for generation of a synthesised data stream of the second data type 20 can be performed in any suitable way using any suitable method.

In examples, the one or more neural networks can be trained and/or prepared in any suitable way for synthesis of data. For example, one or more CGANs 38 can be trained and/or prepared in any suitable way for synthesis of data.

Reference is made to FIG. 9.

FIG. 9 illustrates an example of training of a neural network for the synthesis of data.

The example of FIG. 9 relates to the training of a CGAN 38. However, in examples and suitable neural network can be used.

In the example of FIG. 9, the training of the CGAN involves the joint training of two distinct neural networks, a generator 42 and a discriminator 46.

In the example of FIG. 9, The generator 42 is tasked with producing synthetic data from random noise in input or other data, for example data from one or more other sensors 16.

In the example of FIG. 9, the discriminator 46 takes in input the synthetic data from the generator 42 and real sensor data, one at the time, and tries to distinguish which sample is real and which is synthetic.

By training both networks at the same time they can iteratively improve each other: while the discriminator 46 gets better at spotting synthetic data, the generator 42 gets better at deceiving the discriminator 46.

Typically, at training time the generator 42 minimises the function:

$$\log(1-D(G(z)))$$

Where G(z) is the data generated from the generator 42 with input z and D(G(z)) is the discriminators probability that the generated data is real. The lower the value of this function the better the generator 42 is at creating data that is classified as real by the discriminator 46.

The discriminator 46 instead maximises the function:

$$\log(D(x))+\log(1-D(G(z)))$$

Where D(x) is the discriminator's probability that real data x is indeed real. The higher the value of this function the better the discriminator 46 is at classifying as real, actual real data (first term) and data generated from the generator 42 (second term).

After the training the discriminator 46 can be discarded and the generator 42 is used at runtime to generate synthetic data 22.

In examples, any suitable data can be used to train the generator 42 to synthesise data.

In examples, instead of using random noise to train a GAN, data from other sensors 16 is used to condition the creation of synthetic data from the generator 42.

Hence, in examples data from multiple sensors 16 is used to train the generator 42 and discriminator 46.

Considering the example of generating PPG data, clean PPG data which is first fed to the discriminator 46 and used to compare against generated data. Data from other correlated sensors, for example motion data and ECG data, is fed to the generator 42 and used as prior to condition the generation of synthetic PPG data.

In example, motion data can be enough to condition the generation of synthetic data, however the inclusion of additional modalities, for example, ECG or historical data, improves the capability of the generator at producing realistic data.

In examples, any suitable data-supervised approach can be used to train the generator 42 to produce data.

In examples, the architecture of the generator 42 can use any suitable neural network layers such as convolutions, fully connected and so on.

Referring back to FIG. 3, in examples method 300 comprises replacing at least the data portion 12 of the input sensor data stream 14 with the generated at least one stream of the second, different data type 20.

Accordingly, in examples, the data portion 12 of the input sensor data stream 14 can be replaced with, for example, filtered and/or synthesised data based, at least in part, on the quality of the data portion 12. This allows, for example, for bad and/or missing data to be improved for use in one or more downstream determinations and/or for use by one or more downstream applications.

In examples, a modified input sensor data stream 14 comprising at least one replaced data portion is passed to one or more downstream applications.

In examples, method 300 can be performed on any suitable number of data portions 12 of an input sensor data stream 14. For example, each data portion 12 of the input sensor data stream 14 can be analysed for possible replacement with, for example, filtered and/or synthesised data based, at least in part, on the determined quality of each data portion 12.

As used herein, the term data can be considered to include data and/or information.

Examples of the disclosure are advantageous and/or provide technical benefits.

For example, examples of the disclosure improve poor quality sensor signals before they are fed to downstream models and/or applications thus feeding the models and/or applications with good quality data. This, for example, lifts the need for increased robustness and complexity at the model and/or application level.

Additionally, or alternatively, examples of the disclosure make use of correlations between data of a first type, such as motion data, with noise generated in data from a sensor to act as a reference signal and also correlations with the data from the sensor itself to allow for synthesis of replacement data.

For example, examples of the disclosure can use motion data coming from an IMU to detect and quantify the amount of noise and artifacts introduced by the user's motion and filter them out from the sensor readings; and to condition the generation of synthetic bio-signal data based on the current motion status when the raw sensor data cannot be recovered with standard techniques or is it missing completely.

Additionally, or alternatively, examples of the disclosure also leverage correlations with other sensor data to generate good quality synthetic data as appropriate.

Examples of the disclosure also provide for low latency to, for example, provide applications with real time data.

Examples of the disclosure also provide for transparency for downstream applications. For example, a downstream application that is expecting PPG data will receive seamless, good-quality PPG data even though the data from the sensor might be of poor quality or missing.

Similarly, examples of the disclosure provide for transparency to a user. In examples a user can be a person observing an output or a machine that makes use of the data.

Figure 7:
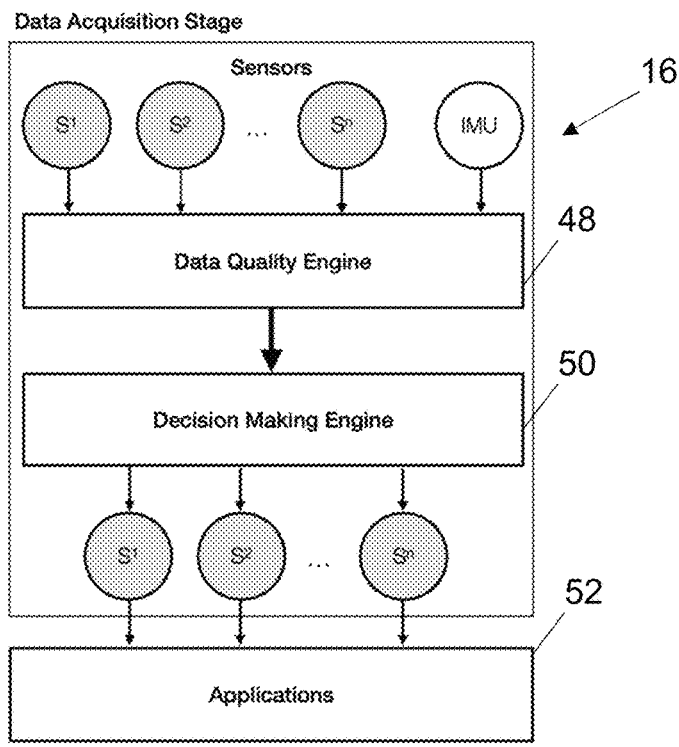
FIG. 7 shows another example of the subject matter described herein.

FIG. 7 illustrates an example overview of some, but not necessarily all, examples of the disclosure.

FIG. 7 illustrates an example of a two-phase algorithm.

In the example of FIG. 7, first, a data quality engine 48 detects poor quality/missing data coming from different bio-sensors 16 (referred to as S1 . . . Sn).

To do this, in the example of FIG. 7, the data quality engine 48 relies on motion status information collected with an onboard IMU (Inertial Measurement Unit).

Then, in the example of FIG. 7, a decision making engine 50 selects the best data-cleaning or data-synthesis strategy, based on the outcomes of the previous block, and produces cleaner sensor streams that can be used by applications 52 in later stages of the pipeline.

To provide low latency, examples of the disclosure are optimized to increase the quality of corrupted readings and synthetize missing data before the end of the overlapping period between two consecutive windows.

In examples this is achieved by relying on efficient filtering techniques and use of conditional generative adversarial networks (CGAN) 38, applying them to the sensory domain.

Examples of the disclosure operate at the data acquisition stage, hence examples are transparent for software components that work at later stages, for example machine learning models or data transmission components.

FIG. 8 illustrates example operation according to examples of the disclosure.

The example of FIG. 8 shows a simplified view of signals coming from an ear-worn device which includes an IMU, a PPG and an ECG sensor.

In the illustrated example, it is assumed that the user wearing the device has a resting heart rate of 60 beats per minute (bpm) or 1 Hz (first section of the plot), runs for a certain period (central part of the figure) and then stops. The user's heart rate increases while running and then takes some time to get back to 60 bpm.

In the first section of FIG. 8 the user is not moving hence the magnitude computed from the IMU is low and its frequency is also low (that is, 0.1 Hz). This informs the system that the PPG and ECG raw data are likely to be clean, hence no filtering is required.

When the user starts running (central part of the figure) this causes deformations of the ear canal which negatively affect the PPG sensor readings while affect the ECG sensor to a lesser degree.

The system detects that the PPG is affected by the user's motion because its frequency is now aligned with the IMU frequency. This does not happen for the ECG because, in this example, the ECG is less affected by motion. At this point the system combines motion data with ECG data to synthetise a clean version of the PPG data while the user is running.

In the example of FIG. 8, the ECG data has been assumed to be not affected by motion and the system can incorporate both motion and other sensors' data (deemed to be clean or at least less affected) to synthetise new sensor data.

However, in examples, the system can also synthetise clean data relying only on motion signals and historical data. Similarly, comparing signals' frequencies to determine if a sensor is affected by noise is merely an example metric that the system can use but it is not limited to that.

FIG. 10A illustrates an example of a controller 1030. The controller 1030 can be used in an apparatus, such as an apparatus 10 of FIG. 1 and/or FIG. 2. In examples controller 1030 can be considered an apparatus 1030.

Implementation of a controller 1030 may be as controller circuitry. The controller 1030 may be implemented in hardware alone, have certain aspects in software including firmware alone or can be a combination of hardware and software (including firmware).

As illustrated in FIG. 10A the controller 1030 may be implemented using instructions that enable hardware functionality, for example, by using executable instructions of a computer program 1036 in a general-purpose or special-purpose processor 1032 that may be stored on a computer readable storage medium (disk, memory etc) to be executed by such a processor 1032.

The processor 1032 is configured to read from and write to the memory 1034. The processor 1032 may also comprise an output interface via which data and/or commands are output by the processor 1032 and an input interface via which data and/or commands are input to the processor 1032.

The memory 1034 stores a computer program 1036 comprising computer program instructions (computer program code) that controls the operation of the apparatus when loaded into the processor 1032. The computer program instructions, of the computer program 1036, provide the logic and routines that enables the apparatus to perform the methods illustrated in FIGS. 3 and/or 4 and/or 5 and/or 6 and/or 7 and/or 8. The processor 1032 by reading the memory 1034 is able to load and execute the computer program 1036.

The apparatus therefore comprises:
at least one processor 1032; and
at least one memory 1034 including computer program code
the at least one memory 1034 and the computer program code configured to, with the at least one processor 1032, cause the apparatus at least to perform:
  determining a quality of a data portion of an input sensor data stream based, at least in part, on data of a first data type;
  determining between, at least, generation of two or more streams of a second, different data type including at least one synthesised data stream of the second data type, wherein the determining between generation of two or more streams of a second, different data type is based, at least in part, on the determined quality and wherein the synthesis is based, at least in part, on the data of the first data type; and
  causing generation of at least one stream of the second, different data type based, at least in part, on the determination between generation of two or more streams of the second, different data type.

As illustrated in FIG. 10A, the computer program 1036 may arrive at the apparatus via any suitable delivery mechanism 1062. The delivery mechanism 1062 may be, for example, a machine readable medium, a computer-readable medium, a non-transitory computer-readable storage medium, a computer program product, a memory device, a record medium such as a Compact Disc Read-Only Memory (CD-ROM) or a Digital Versatile Disc (DVD) or a solid state memory, an article of manufacture that comprises or tangibly embodies the computer program 1036. The delivery mechanism may be a signal configured to reliably transfer the computer program 1036. The apparatus may propagate or transmit the computer program 1036 as a computer data signal.

Computer program instructions for causing an apparatus to perform at least the following or for performing at least the following:
  determining a quality of a data portion of an input sensor data stream based, at least in part, on data of a first data type;
  determining between, at least, generation of two or more streams of a second, different data type including at least one synthesised data stream of the second data type, wherein the determining between generation of two or more streams of a second, different data type is based, at least in part, on the determined quality and wherein the synthesis is based, at least in part, on the data of the first data type; and
  causing generation of at least one stream of the second, different data type based, at least in part, on the determination between generation of two or more streams of the second, different data type.

The computer program instructions may be comprised in a computer program, a non-transitory computer readable medium, a computer program product, a machine readable medium. In some but not necessarily all examples, the computer program instructions may be distributed over more than one computer program.

Although the memory 1034 is illustrated as a single component/circuitry it may be implemented as one or more separate components/circuitry some or all of which may be integrated/removable and/or may provide permanent/semi-permanent/dynamic/cached storage.

In examples the memory 1034 comprises a random-access memory 1058 and a read only memory 1060. In examples the computer program 1136 can be stored in the read only memory 1058. See, for example, FIG. 10B In examples the memory 1034 can be split into random access memory 1058 and read only memory 1060.

Although the processor 1032 is illustrated as a single component/circuitry it may be implemented as one or more separate components/circuitry some or all of which may be integrated/removable. The processor 1032 may be a single core or multi-core processor.

References to 'computer-readable storage medium', 'computer program product', 'tangibly embodied computer program' etc. or a 'controller', 'computer', 'processor' etc. should be understood to encompass not only computers having different architectures such as single/multi-processor architectures and sequential (Von Neumann)/parallel architectures but also specialized circuits such as field-programmable gate arrays (FPGA), application specific circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term 'circuitry' may refer to one or more or all of the following:
(a) hardware-only circuitry implementations (such as implementations in only analogue and/or digital circuitry) and
(b) combinations of hardware circuits and software, such as (as applicable):
(i) a combination of analogue and/or digital hardware circuit(s) with software/firmware and
(ii) any portions of hardware processor(s) with software (including digital signal processor(s)), software, and memory(ies) that work together to cause an apparatus, such as a mobile phone or server, to perform various functions and
(c) hardware circuit(s) and or processor(s), such as a microprocessor(s) or a portion of a microprocessor(s), that requires software (e.g. firmware) for operation, but the software may not be present when it is not needed for operation.

This definition of circuitry applies to all uses of this term in this application, including in any claims. As a further example, as used in this application, the term circuitry also covers an implementation of merely a hardware circuit or processor and its (or their) accompanying software and/or firmware. The term circuitry also covers, for example and if applicable to the particular claim element, a baseband integrated circuit for a mobile device or a similar integrated circuit in a server, a cellular network device, or other computing or network device.

The blocks illustrated in the FIGS. 3 and/or 4 and/or 5 and/or 6 and/or 7 and/or 8 may represent steps in a method and/or sections of code in the computer program 1036. The illustration of a particular order to the blocks does not necessarily imply that there is a required or preferred order for the blocks and the order and arrangement of the block may be varied. Furthermore, it may be possible for some blocks to be omitted.

Where a structural feature has been described, it may be replaced by means for performing one or more of the functions of the structural feature whether that function or those functions are explicitly or implicitly described.

Thus, the apparatus can, in examples, comprise means for:
    determining a quality of a data portion of an input sensor data stream based, at least in part, on data of a first data type;
    determining between, at least, generation of two or more streams of a second, different data type including at least one synthesised data stream of the second data type, wherein the determining between generation of two or more streams of a second, different data type is based, at least in part, on the determined quality and wherein the synthesis is based, at least in part, on the data of the first data type; and
    causing generation of at least one stream of the second, different data type based, at least in part, on the determination between generation of two or more streams of the second, different data type.

In examples, an apparatus can comprise means for performing one or more methods, and/or at least part of one or more methods, as disclosed herein.

In examples, an apparatus can be configured to perform one or more methods, and/or at least part of one or more methods, as disclosed herein.

The systems, apparatus, methods and computer programs may use machine learning which can include statistical learning. Machine learning is a field of computer science that gives computers the ability to learn without being explicitly programmed. The computer learns from experience E with respect to some class of tasks T and performance measure P if its performance at tasks in T, as measured by P, improves with experience E. The computer can often learn from prior training data to make predictions on future data. Machine learning includes wholly or partially supervised learning and wholly or partially unsupervised learning. It may enable discrete outputs (for example classification, clustering) and continuous outputs (for example regression). Machine learning may for example be implemented using different approaches such as cost function minimization, artificial neural networks, support vector machines and Bayesian networks for example. Cost function minimization may, for example, be used in linear and polynomial regression and K-means clustering. Artificial neural networks, for example with one or more hidden layers, model complex relationship between input vectors and output vectors. Support vector machines may be used for supervised learning. A Bayesian network is a directed acyclic graph that represents the conditional independence of a number of random variables.

The above described examples find application as enabling components of: automotive systems; telecommunication systems; electronic systems including consumer electronic products; distributed computing systems; media systems for generating or rendering media content including audio, visual and audio visual content and mixed, mediated, virtual and/or augmented reality; personal systems including personal health systems or personal fitness systems; navigation systems; user interfaces also known as human machine interfaces; networks including cellular, non-cellular, and optical networks; ad-hoc networks; the internet; the internet of things; virtualized networks; and related software and services.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one" or by using "consisting".

In this description, reference has been made to various examples. The description of features or functions in relation to an example indicates that those features or functions are present in that example. The use of the term 'example' or 'for example' or 'can' or 'may' in the text denotes, whether explicitly stated or not, that such features or functions are present in at least the described example, whether described as an example or not, and that they can be, but are not necessarily, present in some of or all other examples. Thus 'example', 'for example', 'can' or 'may' refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example as part of a working combination but does not necessarily have to be used in that other example.

Although examples have been described in the preceding paragraphs with reference to various examples, it should be appreciated that modifications to the examples given can be made without departing from the scope of the claims.

Features described in the preceding description may be used in combinations other than the combinations explicitly described above.

Although functions have been described with reference to certain features, those functions may be performable by other features whether described or not.

Although features have been described with reference to certain examples, those features may also be present in other examples whether described or not.

The term 'a' or 'the' is used in this document with an inclusive not an exclusive meaning. That is any reference to X comprising a/the Y indicates that X may comprise only one Y or may comprise more than one Y unless the context clearly indicates the contrary. If it is intended to use 'a' or 'the' with an exclusive meaning, then it will be made clear in the context. In some circumstances the use of 'at least one' or 'one or more' may be used to emphasis an inclusive meaning but the absence of these terms should not be taken to infer any exclusive meaning.

The presence of a feature (or combination of features) in a claim is a reference to that feature or (combination of features) itself and also to features that achieve substantially the same technical effect (equivalent features). The equivalent features include, for example, features that are variants and achieve substantially the same result in substantially the same way. The equivalent features include, for example, features that perform substantially the same function, in substantially the same way to achieve substantially the same result.

In this description, reference has been made to various examples using adjectives or adjectival phrases to describe characteristics of the examples. Such a description of a characteristic in relation to an example indicates that the characteristic is present in examples exactly as described and is present in other examples substantially as described.

Whilst endeavouring in the foregoing specification to draw attention to those features believed to be of importance it should be understood that the Applicant may seek protection via the claims in respect of any patentable feature or combination of features hereinbefore referred to and/or shown in the drawings whether or not emphasis has been placed thereon.

We claim:

1. An apparatus comprising:
   at least one processor; and
   at least one memory including computer program code, the at least one memory and the computer program code configured to, with the at least one processor, cause the apparatus at least to perform:
   determining a quality of a data portion of an input sensor data stream based, at least in part, on data of a first data type;
   determining, based, at least in part, on the determined quality, which at least one stream of between, at least, generation of two or more streams of a second, different data type to generate, wherein the two or more streams of the second, different data type include at least one synthesised data stream of the second data type, wherein the determining between generation of two or more streams of a second, different data type is based, at least in part, on the determined quality and wherein the synthesis is based, at least in part, on the data of the first data type; and
   causing generation of the at least one stream of the second, different data type based, at least in part, on the determination between generation of which at least one stream of two or more streams of the second, different data type to generate.

2. An apparatus as claimed in claim 1, wherein determining between generation of which at least one stream of two or more streams of a second, different data type comprises determining between generation of, at least, a filtered data stream of the second data type and a synthesised data stream of the second data type, wherein the filtered data stream is based, at least in part, on the data portion of the input sensor data stream and the synthesised data stream is not based on the data portion of the input sensor data stream.

3. An apparatus as claimed in claim 1, wherein the at least one memory and the computer program code are further configured to, with the at least one processor, cause the apparatus at least to perform: generating a filtered or synthesised data stream of the second data type based, at least in part, on the determination of which at least one stream between generation of two or more streams of the second data type, wherein generating a filtered data stream comprises filtering data from the data portion of the input sensor data stream and wherein generating a synthesised data stream comprises generating new data not based on the data portion of the input sensor data stream.

4. An apparatus as claimed in claim 1, wherein the at least one memory and the computer program code are further configured to, with the at least one processor, cause the apparatus at least to perform:
   replacing at least the data portion of the input sensor data stream with a generated stream of the second, different data type.

5. An apparatus as claimed in claim 1, wherein determining the quality of the data portion of an input sensor data stream comprises determining the quality of the data portion of the input sensor data stream based, at least in part, on a corresponding data portion of the first data type.

6. An apparatus as claimed in claim 1, wherein determining the quality of the data portion of an input sensor data stream comprises comparing one or more frequency components of the data portion of the input sensor data stream and the data of the first data type.

7. An apparatus as claimed in claim 1, wherein generation of a synthesised data stream of the second data type is based, at least in part, on at least one of: one or more previous data portions of the input sensor data stream and data from one or more different sensors.

8. An apparatus as claimed in claim 1, wherein the first data type comprises motion data and the second data type comprises biosignal data.

9. An apparatus as claimed in claim 8, wherein the second data type comprises heart rate data and the input sensor data stream is from at least one photoplethysmography sensor.

10. An electronic device comprising an apparatus as claimed in claim 1 and at least one input configured to receive the input sensor data stream.

11. A method comprising:
    determining a quality of a data portion of an input sensor data stream based, at least in part, on data of a first data type;
    determining, based, at least in part, on the determined quality, which at least one stream of between, at least, generation of two or more streams of a second, different data type to generate, wherein the two or more streams of the second, different data type include at least one synthesised data stream of the second data type, wherein the determining between generation of two or more streams of a second, different data type is based, at least in part, on the determined quality and wherein the synthesis is based, at least in part, on the data of the first data type; and
    causing generation of the at least one stream of the second, different data type based, at least in part, on the determination between generation of which at least one stream of two or more streams of the second, different data type to generate.

12. A method as claimed in claim 11, wherein determining between generation of which at least one stream of two or more streams of a second, different data type comprises determining between generation of, at least, a filtered data stream of the second data type and a synthesised data stream of the second data type, wherein the filtered data stream is based, at least in part, on the data portion of the input sensor data stream and the synthesised data stream is not based on the data portion of the input sensor data stream.

13. A method as claimed in claim 11, further comprising:
replacing at least the data portion of the input sensor data stream with a generated stream of the second, different data type.

14. A method as claimed in claim 11, further comprising generating a filtered or synthesised data stream of the second data type based, at least in part, on the determination of which at least one stream between generation of two or more streams of the second data type, wherein generating a filtered data stream comprises filtering data from the data portion of the input sensor data stream and wherein generating a synthesised data stream comprises generating new data not based on the data portion of the input sensor data stream.

15. A method as claimed in claim 11, wherein determining the quality of the data portion of an input sensor data stream comprises determining the quality of the data portion of the input sensor data stream based, at least in part, on a corresponding data portion of the first data type.

16. A method as claimed in claim 11, wherein determining the quality of the data portion of an input sensor data stream comprises comparing one or more frequency components of the data portion of the input sensor data stream and the data of the first data type.

17. A method as claimed in claim 11, wherein generation of a synthesised data stream of the second data type is based, at least in part, on at least one of: one or more previous data portions of the input sensor data stream and data from one or more different sensors.

18. A method as claimed in claim 11, wherein the first data type comprises motion data and the second data type comprises biosignal data.

19. A non-transitory computer readable medium comprising program instructions for causing an apparatus to perform at least the following:
determining a quality of a data portion of an input sensor data stream based, at least in part, on data of a first data type;
determining, based, at least in part, on the determined quality, which at least one stream of between, at least, generation of two or more streams of a second, different data type to generate, wherein the two or more streams of the second, different data type include at least one synthesised data stream of the second data type, wherein determining between generation of two or more streams of a second, different data type is based, at least in part, on the determined quality and wherein the synthesis is based, at least in part, on the data of the first data type; and
causing generation of the at least one stream of the second, different data type based, at least in part, on the determination between generation of which at least one stream of two or more streams of the second, different data type to generate.

20. A non-transitory computer readable medium comprising program instructions as claimed in claim 19, wherein determining between generation of which at least one stream of two or more streams of a second, different data type comprises determining between generation of, at least, a filtered data stream of the second data type and a synthesised data stream of the second data type, wherein the filtered data stream is based, at least in part, on the data portion of the input sensor data stream and the synthesised data stream is not based on the data portion of the input sensor data stream.

* * * * *

UNITED STATES PATENT AND TRADEMARK OFFICE
CERTIFICATE OF CORRECTION

| | | |
|---|---|---|
| PATENT NO. | : 12,329,542 B2 | Page 1 of 1 |
| APPLICATION NO. | : 17/892806 | |
| DATED | : June 17, 2025 | |
| INVENTOR(S) | : Alessandro Montanari et al. | |

It is certified that error appears in the above-identified patent and that said Letters Patent is hereby corrected as shown below:

On the Title Page

Item (71), Applicant, Line 1, delete "Cambridge, GA (US)" and insert -- Cambridge (GB) --, therefor.

Signed and Sealed this
Ninth Day of September, 2025

Coke Morgan Stewart
*Acting Director of the United States Patent and Trademark Office*